United States Patent
Tazawa

(10) Patent No.: US 12,178,747 B2
(45) Date of Patent: Dec. 31, 2024

(54) OPHTHALMIC FORCEPS

(71) Applicant: MANI, INC., Utsunomiya (JP)

(72) Inventor: Yoshiyuki Tazawa, Utsunomiya (JP)

(73) Assignee: MANI, INC., Tochigi (JP)

( * ) Notice: Subject to any disclaimer, the term of this patent is extended or adjusted under 35 U.S.C. 154(b) by 112 days.

(21) Appl. No.: 17/022,854

(22) Filed: Sep. 16, 2020

(65) Prior Publication Data
US 2021/0093480 A1    Apr. 1, 2021

(30) Foreign Application Priority Data
Sep. 26, 2019  (JP) .................. 2019-175553

(51) Int. Cl.
*A61B 17/29*    (2006.01)
*A61F 9/007*    (2006.01)

(52) U.S. Cl.
CPC ............. *A61F 9/007* (2013.01); *A61B 17/29* (2013.01)

(58) Field of Classification Search
CPC ......... A61B 17/28; A61B 17/29; A61B 17/30; A61B 17/282; A61B 17/2812; A61B 17/2841; A61B 2017/2926; A61B 2017/2936; A61F 9/007; A61F 9/00736
See application file for complete search history.

(56) References Cited

U.S. PATENT DOCUMENTS

| | | | |
|---|---|---|---|
| 5,222,973 A | 6/1993 | Sharpe et al. | |
| 5,527,313 A * | 6/1996 | Scott | A61B 18/1442 606/41 |
| 9,827,141 B2 | 11/2017 | Schaller et al. | |
| 10,092,168 B1 | 10/2018 | Huttner et al. | |
| 10,406,027 B2 | 9/2019 | Grueebler et al. | |
| 2008/0188877 A1 | 8/2008 | Hickingbotham | |
| 2011/0015669 A1 | 1/2011 | Corcosteugi | |
| 2011/0295289 A1 | 12/2011 | Andre | |
| 2014/0121697 A1 * | 5/2014 | Scheller | A61B 17/30 606/207 |

(Continued)

FOREIGN PATENT DOCUMENTS

| | | |
|---|---|---|
| CN | 205849641 U | 1/2017 |
| CN | 108095805 A | 6/2018 |

(Continued)

OTHER PUBLICATIONS

European Search Report dated Mar. 15, 2021 issued in European Patent Application No. EP 20197410.2.

(Continued)

*Primary Examiner* — Erich G Herbermann
(74) *Attorney, Agent, or Firm* — RANKIN, HILL & CLARK LLP

(57) ABSTRACT

Ophthalmic forceps include: a tubular body; a pair of neck portions; a pair of slit formation portions provided on a tip end side of the neck portions; a pair of gripping portions provided on a tip end side of the slit formation portions; and substantially S-shaped portions formed at portions extending from the neck portions to the slit formation portions. When the tubular body slides to house an entirety of the neck portions in an inner cavity of the tubular body, gripping surfaces of the gripping portions are in surface contact with each other, and a slit is formed between the pair of slit formation portions.

3 Claims, 4 Drawing Sheets

(56) References Cited

U.S. PATENT DOCUMENTS

| | | |
|---|---|---|
| 2014/0135820 A1 | 5/2014 | Schaller et al. |
| 2014/0172010 A1* | 6/2014 | Vezzu ................. A61B 17/285 606/207 |
| 2014/0379024 A1 | 12/2014 | Schaller et al. |
| 2015/0238355 A1 | 8/2015 | Vezzu et al. |
| 2015/0359669 A1 | 12/2015 | Grueebler et al. |
| 2017/0086871 A1* | 3/2017 | Scheller ................. A61F 9/007 |
| 2017/0348013 A1 | 12/2017 | Mottola et al. |
| 2018/0368911 A1 | 12/2018 | van Overdam |
| 2019/0000670 A1 | 1/2019 | Grueebler |
| 2019/0357928 A1* | 11/2019 | Hassan .............. A61B 17/2841 |

FOREIGN PATENT DOCUMENTS

| | | |
|---|---|---|
| CN | 109820640 A | 5/2019 |
| CN | 209377865 U | 9/2019 |
| DE | 102009033015 A1 | 1/2011 |
| JP | 2017-506111 A | 3/2017 |
| JP | 2017517326 A | 6/2017 |
| RU | 15644 U1 | 11/2000 |
| RU | 2319475 C2 | 3/2008 |
| RU | 2011-135848 A | 3/2013 |
| RU | 185416 U1 | 12/2018 |
| TW | 2014-34431 A | 9/2014 |
| TW | 2015-21665 A | 6/2015 |
| WO | 2010-126076 A1 | 11/2010 |
| WO | 2013120491 A1 | 8/2013 |
| WO | 2020/179550 A1 | 9/2020 |

OTHER PUBLICATIONS

Office Action issued on May 7, 2021 for the corresponding Taiwanese Patent Application No. 109133205.

International Search Report dated May 26, 2020 issued in PCT/JP2020/007549 (U.S. Appl. No. 17/286,305).

Australian Office Action dated Apr. 8, 2021 issued in Australian Patent Application No. 2020233742.

Pamphlet "The Benchmark for Vitreoretinal Single-Use Instruments".

Notice of Opposition dated Jan. 5, 2023 for the corresponding European Patent Application No. 20197410.2.

Office Action issued on Nov. 30, 2023 for the corresponding U.S. Appl. No. 17/286,305.

Japanese Office Action (JPOA) dated Jul. 28, 2022 for Japanese Patent Application No. 2021-503987; English Machine Translation.

* cited by examiner

OPHTHALMIC FORCEPS

BACKGROUND

1. Technical Field

One aspect of the present disclosure relates to ophthalmic forceps used for an ophthalmic surgery.

2. Related Art

In ophthalmic surgeries such as a vitreous surgery, a cataract surgery, and a glaucoma surgery, eye tissues or the like are gripped and treated. In these ophthalmic surgeries, a cannula is first attached to an eyeball when an ophthalmic surgery instrument and the like are used inside the eyeball. The ophthalmic surgery instrument and the like are inserted through the cannula (see, e.g., WO 2010/126076). One example of the ophthalmic surgery instrument is ophthalmic forceps for gripping an eye tissue such as a vitreous body for treatment.

FIG. 5 is a view upon use of general ophthalmic forceps. A general cannula 40 attached to an eyeball E in a vitreous surgery includes a metal pipe and a resin base fitted in the vicinity of a base end portion of the pipe.

The ophthalmic forceps 100 have, on a tip end side thereof, a forceps portion 30 for gripping a vitreous body. The forceps portion 30 is inserted into the eyeball E through the cannula 40. A tip end of the forceps portion 30 is gripping portions 34, and neck portions 32 are formed continuously from the gripping portions 34. Further, a base-end-side portion with respect to the neck portions 32 is housed in an inner cavity of a tubular body 31. The tubular body 31 is, together with the forceps portion 30, inserted into the eyeball E. Thus, an extremely-thin material is used as the material of the tubular body 31. In some cases, the outside of the tubular body 31 is reinforced by a reinforcing sleeve 33 to reduce bending of the tubular body 31 outside the cannula 40 during a process.

In a basic configuration of the ophthalmic forceps 100, a body portion 35 is provided outside the tubular body 31 through other components. A movement member 37 is provided at a position slidable relative to the body portion 35. The movement member 37 and the tubular body 31 as described herein are connected to each other. When operating portions 36 are closed or opened, the movement member 37 connected to the operating portions 36 through a biasing means such as a plate spring moves in an axial direction relative to the body portion 35. Accordingly, the tubular body 31 connected to the movement member 37 slides in the axial direction. In this manner, the neck portions 32 move in and out of the inner cavity of the tubular body 31. When the neck portions 32 move in the inner cavity of the tubular body 31, the gripping portions 34 are closed. When the neck portions 32 move out of the tubular body 31, the gripping portions 34 are opened. That is, when the operating portions 36 are closed with fingers, the gripping portions 34 of the forceps portion 30 are closed. On the other hand, when the fingers are relaxed to open the operating portions 36, the gripping portions 34 are opened. Note that the ophthalmic forceps 100 are provided with the reinforcing sleeve 33. The reinforcing sleeve 33 is not provided in some cases. Moreover, the movement member 37 may be arranged inside or outside the body portion 35.

As the ophthalmic forceps 100, there are one having gripping surfaces of gripping portions 34 for line contact and one having gripping surfaces of gripping portions 34 for surface contact. FIG. 6 shows a forceps portion of the ophthalmic forceps having the gripping surfaces for line contact and a forceps portion of the ophthalmic forceps having the gripping surfaces for surface contact. The forceps portion 30 having the gripping surfaces 34a for line contact is shown on an upper side, and the forceps portion 30 having the gripping surfaces 34b for surface contact is shown on a lower side. Note that the gripping surface 34b for surface contact becomes closer to the gripping surface 34a for line contact as the area of the gripping surface 34b decreases. Thus, a boundary between surface contact and line contact is not definite. A gripping surface having a shape with a longer length in a width direction of the forceps portion 30 is herein taken as the gripping surface for line contact. On the other hand, a gripping surface having a shape with a longer length in a direction from a tip end to a base end than that in a width direction is taken as the gripping surface for surface contact.

The gripping surface 34b for surface contact has an advantage that gripping force per unit area can be more improved as the shape of the gripping surface is closer to that of the gripping surface for line contact. Thus, for decreasing the gripping surface 34b in size, a slit is sometimes provided on a neck portion 32 side of the gripping surface 34b. With the slit, there is also an advantage that tip end portions of the gripping portions 34 are easily visually checked during a process.

The ophthalmic forceps having the gripping surfaces 34a, 34b for line contact and surface contact are differently used depending on the situation. For example, in a case where a proliferative membrane adheres to a retina, the proliferative membrane near the retina is gripped and pulled up by the gripping portions 34. Thus, the ophthalmic forceps having the gripping surfaces 34a for line contact are suitably used. On the other hand, for gripping a proliferative membrane separated from a retina, it is necessary to remove the proliferative membrane with the proliferative membrane being firmly sandwiched. Thus, the ophthalmic forceps having the gripping surfaces 34b for surface contact are suitably used.

In the ophthalmic forceps having the gripping surfaces 34b for surface contact as described herein, it is difficult to bring the entirety of two gripping surfaces 34b into surface contact with each other with the same level of pressure when the gripping portions 34 are closed by sliding of the tubular body 31. Generally, in many cases, a proliferative membrane or the like are sandwiched by a tip end side of the gripping portions 34. Thus, when the gripping portions 34 are closed, tip-end-side portions of the gripping surfaces 34b first contact each other, and thereafter, base-end-side portions sequentially contact each other. However, when two gripping surfaces 34b contact each other across the entire surfaces by sliding of the tubular body 31, a tip-end-side pressure is lower due to the slit formed at the back of the gripping surfaces 34b. In some cases, a slight clearance is formed on the tip end side.

On this point, the gripping surfaces 34b are preferably in surface contact with each other such that the tip-end-side pressure is held and the pressure is on the entirety of the gripping surfaces 34b. Thus, in any of situations where the proliferative membrane near retina is pulled up and the proliferative membrane separated from the retina is gripped, the ophthalmic forceps having the gripping surfaces 34b for surface contact can be used.

SUMMARY

Ophthalmic forceps include: a tubular body; a pair of neck portions; a pair of slit formation portions provided on a tip end side of the neck portions; a pair of gripping portions provided on a tip end side of the slit formation portions; and substantially S-shaped portions formed at portions extending from the neck portions to the slit formation portions. When the tubular body slides to house an entirety of the neck portions in an inner cavity of the tubular body, gripping surfaces of the gripping portions are in surface contact with each other, and a slit is formed between the pair of slit formation portions, each substantially S-shaped portion includes a first curved portion curving outward from a center axis of the tubular body and a second curved portion curving inward to the center axis of the tubular body and positioned on a gripping portion side, a thickness of each slit formation portion is greater than a thickness of each neck portion, at a position of connection between each neck portion and each slit formation portion, a step at an opposite side to the slit is formed due to a difference in the thickness between the each slit formation portion and the each neck portion, and in a state in which the gripping surfaces are in surface contact with each other, a distance from the center axis of the tubular body to an outer edge of each neck portion at an end surface position of the tubular body is equal to or less than a radius of the inner cavity of the tubular body, and is greater than a distance obtained by subtraction of a height of the step from the radius of the inner cavity of the tubular body.

DETAILED DESCRIPTION

Figure 1:
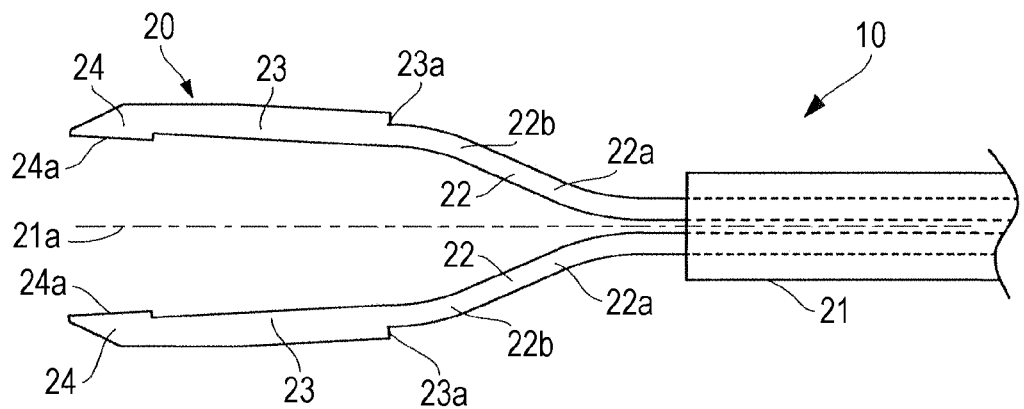
FIG. 1 is an enlarged view of a forceps portion of ophthalmic forceps according to one embodiment of the present disclosure.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

One object of the present disclosure is to provide the following ophthalmic forceps. In the ophthalmic forceps, when gripping portions are closed, gripping surfaces are in surface contact with each other while opening of a tip end side of the gripping surfaces is reduced.

Ophthalmic forceps according to an aspect of the present disclosure (this ophthalmic forceps) include: a tubular body; a pair of neck portions; a pair of slit formation portions provided on a tip end side of the neck portions; a pair of gripping portions provided on a tip end side of the slit formation portions; and substantially S-shaped portions formed at portions extending from the neck portions to the slit formation portions. When the tubular body slides to house an entirety of the neck portions in an inner cavity of the tubular body, gripping surfaces of the gripping portions are in surface contact with each other, and a slit is formed between the pair of slit formation portions, each substantially S-shaped portion includes a first curved portion curving outward from a center axis of the tubular body and a second curved portion curving inward to the center axis of the tubular body and positioned on a gripping portion side, a thickness of each slit formation portion is greater than a thickness of each neck portion, at a position of connection between each neck portion and each slit formation portion, a step at an opposite side to the slit is formed due to a difference in the thickness between the each slit formation portion and the each neck portion, and in a state in which the gripping surfaces are in surface contact with each other, a distance from the center axis of the tubular body to an outer edge of each neck portion at an end surface position of the tubular body is equal to or less than a radius of the inner cavity of the tubular body, and is greater than a distance obtained by subtraction of a height of the step from the radius of the inner cavity of the tubular body. The first curved portion is curving outward from the center axis and the second curved portion is curving inward from the center axis. In other words, the first curved portion has a first direction of curvature away from the center axis and the second curved portion has a second direction of curvature towards the center axis. In still other words, the first curved portion is curved to be convex when viewed from the center axis and the second curved portion is curved to be concave when viewed from the center axis.

The height of the step as described herein may be equal to or less than the thickness of the tubular body.

According to the ophthalmic forceps of the present disclosure, an advantageous effect that when the gripping portions are closed, the gripping surfaces are in surface contact with each other and opening of the tip end side of the gripping surfaces is reduced is provided.

Hereinafter, an embodiment of the present disclosure will be described with reference to the attached drawings.

FIG. 1 is an enlarged view of a forceps portion of ophthalmic forceps according to one embodiment of the present disclosure. Basic motion of the ophthalmic forceps 10 is similar to that in a typical case as described above. That is, a tubular body 21 slides by opening/closing of operating portions, and accordingly, neck portions 22 move in and out of an inner cavity of the tubular body 21. Accordingly, gripping portions 24 are opened/closed. Specifically, when the operating portions are closed with fingers, the gripping portions 24 of the forceps portion 20 are closed. When the fingers are relaxed to open the operating portions, the gripping portions 24 are opened.

The forceps portion 20 of the ophthalmic forceps 10 includes the pair of neck portions 22, a pair of slit formation portions 23 provided on a tip end side of the neck portions 22, and the pair of gripping portions 24 provided on a tip end side of the slit formation portions 23. Note that a back-end-side portion of the forceps portion 20 with respect to the neck portions 22 is not shown. Such a portion is fixed in the vicinity of bases of the operating portions with the portion being inserted into the tubular body 21.

The neck portion 22 as described herein has a substantially S-shaped portion formed by two connected curved shapes. The tubular-body-side curved portion will be referred to as a first curved portion 22a, whereas the gripping-portion-side curved portion will be referred to as a second curved portion 22b. Moreover, the first curved portion 22a is curved such that the portion is leaving the center axis 21a of the tubular body. On the other hand, the second curved portion 22b is curved such that the portion is approaching the center axis 21a of the tubular body. In other words, the center axis 21a of the tubular body is positioned outside the first curved portion 22a and inside the second curved portion 22b.

A gripping surface 24a of the gripping portion 24 is a flat surface of which length in a direction from a tip end to a base end is longer than that in a width direction of the forceps portion 20. The shape of the neck portion 22 is determined such that two gripping surfaces 24a are in surface contact with each other when the gripping portions 24 are closed.

The slit formation portion 23 is provided between the gripping portion 24 and the neck portion 22. The slit formation portion 23 has such a shape that a slit is formed between the pair of slit formation portions 23 when the gripping portions 24 are closed. With such slit formation portions 23, gripping force on the gripping surface 24a per unit area can be increased. Thus, the gripping surface 24a can be designed to have an optimal size. Moreover, since the slit is formed, there is also an advantage that tip ends of the gripping portions 24 are easily visually checked in a process.

At the position of connection between the slit formation portion 23 and the neck portion 22, the slit formation portion 23 and the neck portion 22 are continuously connected to each other on the same plane on a slit side. A step 23a is formed outside. When the gripping portions 24 are closed, the neck portions 22 are housed in the inner cavity of the tubular body 21. Thus, the neck portion 22 has such a thickness that the neck portion 22 is elastically deformable. On the other hand, the slit formation portion 23 preferably has high stiffness to generate sufficient gripping force at the gripping portion 24. Thus, the slit formation portion 23 is formed thicker than the neck portion 22. As a result, the step 23a is formed. Note that the step 23a also has a function as a stopper when the neck portions 22 are housed in the inner cavity of the tubular body 21.

Figure 2:
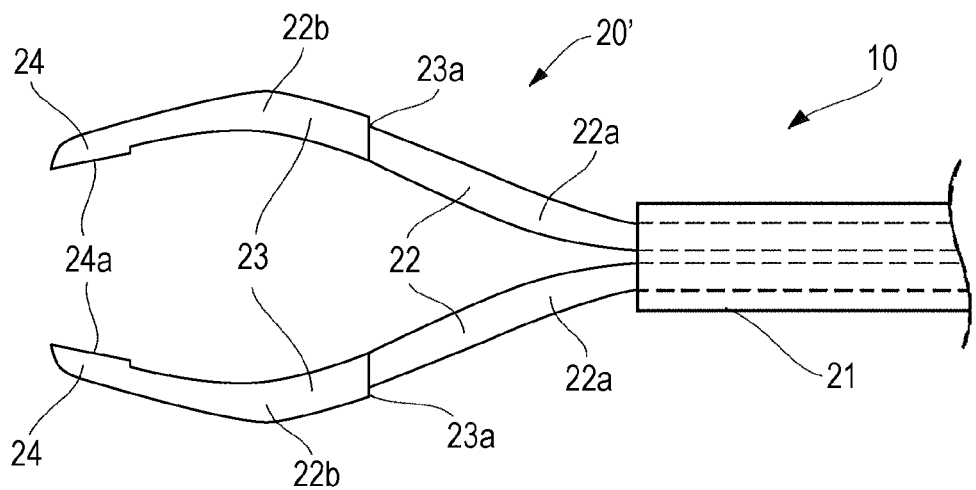
FIG. 2 is an enlarged view of a forceps portion of ophthalmic forceps according to another embodiment of the present disclosure.

Next, FIG. 2 is an enlarged view of a forceps portion of ophthalmic forceps according to another embodiment of the present disclosure. Motion and functions of the forceps portion 20' of FIG. 2 are almost the same as those of the forceps portion 20 of FIG. 1. Note that at the forceps portion 20' of FIG. 2, second curved portions 22b are not provided at neck portions 22, but are provided at slit formation portions 23. That is, a first curved portion 22a formed at the neck portion 22 and the second curved portion 22b formed at the slit formation portion 23 form a portion in a substantially S-shape. Thus, the forceps portion 20 of FIG. 1 and the forceps portion 20' of FIG. 2 are summarized as follows: the substantially S-shaped portion is formed at a portion extending from the neck portion 22 to the slit formation portion 23.

Figure 3A:
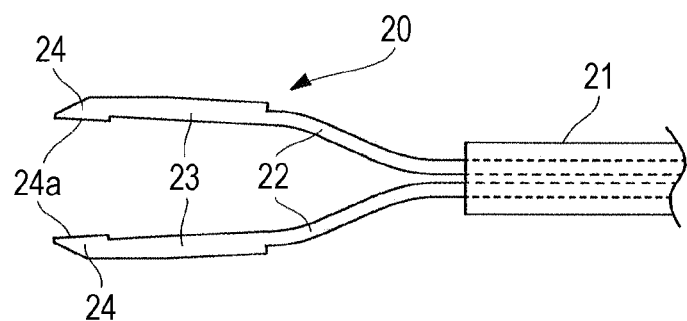
FIGS. 3A to 3C are views for describing movement of the forceps portion, FIG. 3A showing the forceps portion in a state in which gripping portions are opened, FIG. 3B showing the forceps portion in a state in which a tip end side of the gripping portions is slightly closed, and FIG. 3C showing the forceps portion in a state in which the gripping portions are closed.
Figure 3B:
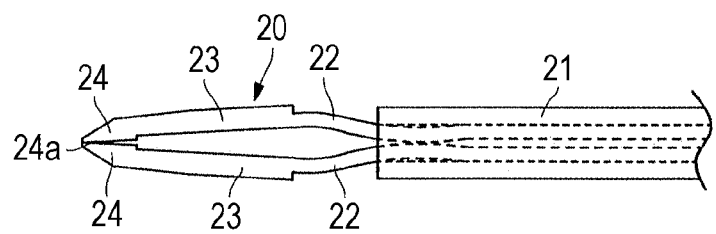
Figure 3C:
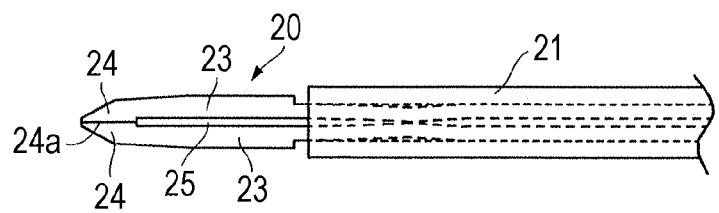

The gripping portions 24 are closed when the neck portions 22 are housed in the inner cavity of the tubular body 21 by sliding of the tubular body 21. Movement of the forceps portion 20 at this point will be described with reference to the figures. Note that the forceps portion 20 of FIG. 1 will be described herein. The same basic movement is also employed in the forceps portion 20' of FIG. 2. FIGS. 3A to 3C are views for describing movement of the forceps portion. FIG. 3A shows the forceps portion 20 in a state in which the gripping portions 24 are opened. FIG. 3B shows the forceps portion 20 in a state in which a tip end side of the gripping portions 24 is slightly closed. FIG. 3C shows the forceps portion 20 in a state in which the gripping portions 24 are closed.

As shown in FIG. 3A, when the neck portions 22 are not housed in the inner cavity of the tubular body 21, the forceps portion 20 is in a state in which the gripping portions 24 are opened. When the tubular body 21 slides from this state to house the first curved portions 22a of the neck portions 22 in the inner cavity of the tubular body 21, the gripping surfaces 24a of the gripping portions 24 come into contact with each other from the tip end side. In this state, the forceps portion 20 is, as shown in FIG. 3B, in a state in which a tip end side of the forceps portion 20 is slightly closed and a tubular body side of the forceps portion 20 is slightly opened.

When the tubular body 21 further slides to house the entirety of the neck portions 22 in the inner cavity of the tubular body 21, the second curved portions 22b (see FIG. 1) act as springs, and accordingly, the gripping surfaces 24a are brought into surface contact with each other.

Thus, the curvature radius of the first curved portion 22a is determined considering that the tip ends of the gripping surfaces 24a contact each other when the first curved portions 22a are housed in the inner cavity of the tubular body 21. Moreover, the curvature radius of the second curved portion 22b is determined considering spring force for bringing the gripping surfaces 24a into surface contact with each other. Note that in addition to such determination on the shape of the neck portion 22, the size of each portion is preferably properly determined. With this configuration, opening of a tip end side of the gripping surfaces 24a with pressure concentration on a back end side of the gripping surfaces 24a when the entirety of the neck portions 22 is housed in the inner cavity of the tubular body 21 can be reduced. The tip end side of the gripping portions 24 is mainly used for, e.g., pulling up a proliferative membrane near a retina. Thus, it is preferred that opening of the tip end side of the gripping surfaces 24a is avoided. For this reason, the size of each portion is preferably determined such that a state in which the gripping surfaces 24a are in surface contact with each other, the tip end side of the gripping surfaces 24a is not opened, and sufficient pressure is on the tip end side of the gripping surfaces 24a is brought when the entirety of the neck portions 22 is housed in the inner cavity of the tubular body 21.

Figure 4:
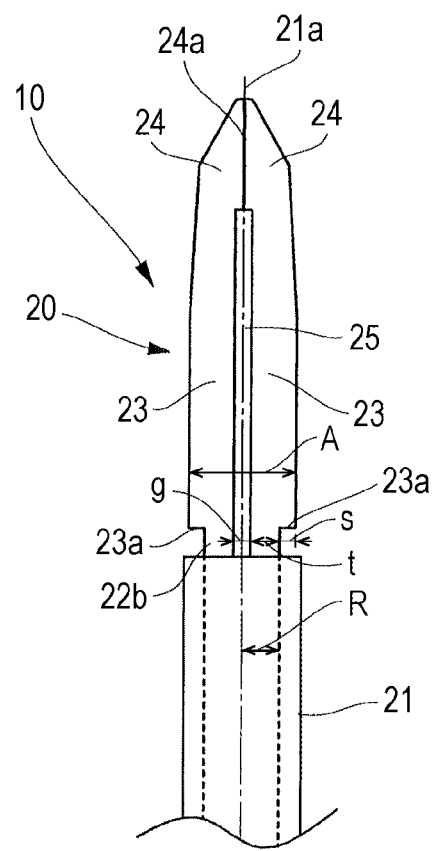
FIG. 4 is a view for describing the forceps portion in a state in which the gripping portions are closed.
Figure 5:
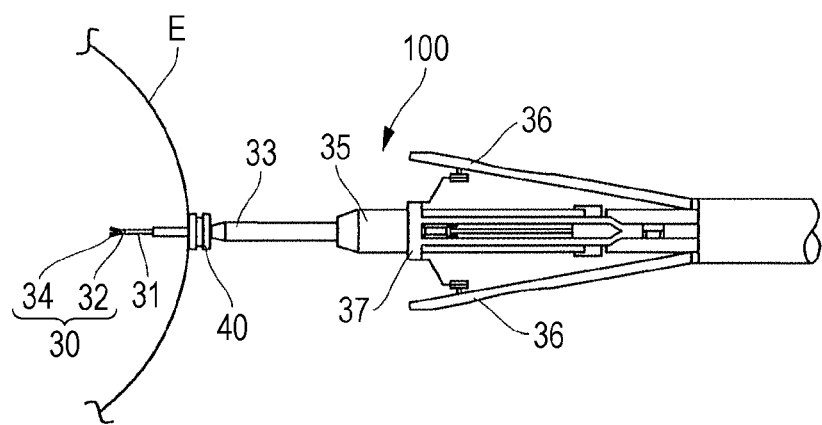
FIG. 5 is a view upon use of general ophthalmic forceps.
Figure 6:
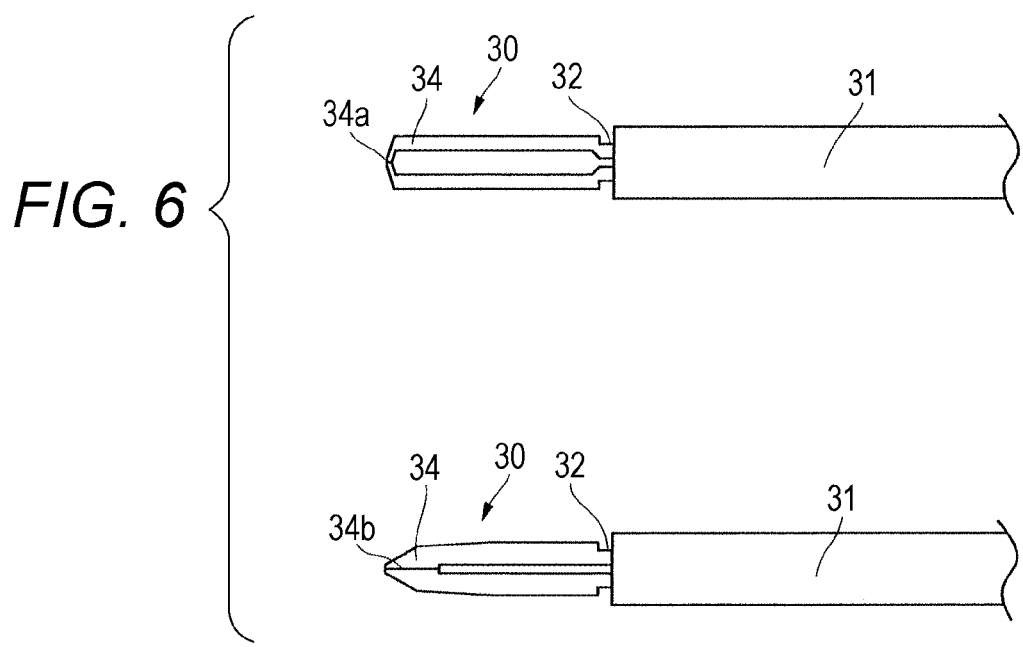
FIG. 6 shows ophthalmic forceps having gripping surfaces for line contact and ophthalmic forceps having gripping surfaces for surface contact.

FIG. 4 is a view for describing the forceps portion 20 in a state in which the gripping portions 24 are closed. The state shown in this figure is a state in which the gripping surfaces 24a are in surface contact with each other. In this state, a distance from the center axis 21a of the tubular body 21 to an outer edge of the neck portion 22 at an end surface position of the tubular body 21, i.e., a distance t+g/2 as the total of the thickness t of the neck portion 22 and the half of a slit width g, is preferably equal to or less than the radius R of the inner cavity of the tubular body 21.

If the distance as the total of the thickness t of the neck portion 22 and the half of the slit width g is greater than the radius R of the inner cavity of the tubular body 21, when the neck portions 22 are housed in the inner cavity of the tubular body 21, the neck portions 22 are not housed straight, but are housed inclined. Due to such inclination, the gripping portions 24 are inclined and the tip end side of the gripping surface 24a is opened, and for this reason, it is difficult to bring the gripping surfaces 24a into surface contact with each other. That is, as long as $t+g/2 \leq R$ is not satisfied, it is difficult to bring the gripping surfaces 24a into surface contact with each other.

Moreover, in a state in which the gripping surfaces 24a are in surface contact with each other, the width A of the forceps portion 20 at the end surface position of the tubular body 21 is a distance between outer edges of the slit formation portions 23. The width A is preferably greater than the diameter (2R) of the inner cavity of the tubular body 21. This is because in a case where the width A is equal to or less than the diameter (2R) of the inner cavity of the tubular body 21, there is a probability that even the slit formation portions 23 are housed in the inner cavity of the tubular body 21 by sliding of the tubular body 21. That is, 2R<A is preferably satisfied.

Using the thickness t of the second curved portion 22b, the height s of the step, and the slit width g, the width A described herein is represented by A=2t+2s+g. Thus, a condition expression is 2R<2t+2s+g. When this expression is transformed, R−s<t+g/2 is brought.

In summary, a condition of R−s<t+g/2≤R is preferably satisfied. That is, for surface contact between the gripping surfaces 24a, the distance from the center axis 21a of the tubular body 21 to the outer edge of the neck portion 22 is preferably equal to or less than the radius of the inner cavity of the tubular body 21, and is preferably greater than the distance obtained by subtraction of the height of the step 23a from the radius of the inner cavity of the tubular body 21.

Next, description will be made using specific numerical values. In the case of using the 27-gauge tubular body 21, the diameter (2R) of the inner cavity of the tubular body 21 is 0.30 mm, and the thickness is 0.05 mm. Moreover, the height (s) of the step 23a is equal to or less than the thickness of the tubular body 21, and is equal to or greater than 0.03 mm and equal to or less than 0.05 mm so that the step 23a can function as the stopper. Note that this range of the step 23a is also applicable in the case of the tubular bodies 21 with other sizes.

From description above, the condition expression is 0.12<t+g/2≤0.15. Thus, the thickness t of the neck portion 22 and the slit width g are determined such that this expression is satisfied and sufficient gripping forces is generated, and therefore, the ophthalmic forceps 10 configured such that when the gripping portions 24 are closed, the gripping surfaces 24a are in surface contact with each other and the tip end side of the gripping surfaces 24a is not opened can be obtained.

The ophthalmic forceps according to the present embodiment may be the following first ophthalmic forceps. The first ophthalmic forceps include a tubular body, a pair of neck portions, a pair of slit formation portions provided on a tip end side of the neck portions, and a pair of gripping portions provided on a tip end side of the slit formation portions. When the tubular body slides to house the entirety of the neck portions in an inner cavity of the tubular body, gripping surfaces of the gripping portions are in surface contact with each other, and a slit is formed between the pair of slit formation portions. The ophthalmic forceps include substantially S-shaped portions formed at portions extending from the neck portions to the slit formation portions. Each substantially S-shaped portion has a first curved portion curving outward from the center axis of the tubular body and a second curved portion curving inward to the center axis of the tubular body and positioned on a gripping portion side. The thickness of the slit formation portion is greater than the thickness of the neck portion. At the position of connection between the neck portion and the slit formation portion, a step at an opposite side to the slit is formed due to a difference in the thickness between the slit formation portion and the neck portion. In a state in which the gripping surfaces are in surface contact with each other, a distance from the center axis of the tubular body to an outer edge of the neck portion at an end surface position of the tubular body is equal to or less than the radius of the inner cavity of the tubular body, and is greater than a distance obtained by subtraction of the height of the step from the radius of the inner cavity of the tubular body.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

The invention claimed is:
1. Ophthalmic forceps (10) comprising:
a tubular body (21);
a pair of neck portions (22);
a pair of slit formation portions (23) provided on an end of the neck portions;
a pair of gripping portions (24) provided at a tip end of the ophthalmic forceps; and
substantially S-shaped portions formed at portions extending from the neck portions to the slit formation portions, wherein
the pair of slit formation portions (23) is provided between the pair of neck portions (22) and the pair of gripping portions (24),
a length in a direction from the tip end of the ophthalmic forceps to a base end of gripping surfaces of the pair of gripping portions is longer than a length of the slit formation portions (23) in a width direction,
when the tubular body slides to house the neck portions in an inner cavity of the tubular body, the tip end of the ophthalmic forceps first contact with each other, thereafter the base end of the gripping surfaces sequentially contact with each other, and entire gripping surfaces of the gripping portions are in surface contact with each other, the tip end of the ophthalmic forceps is not opened when an entirety of the neck portion is housed in the inner cavity of the tubular body, and a slit is formed between the pair of slit formation portions,
each substantially S-shaped portion includes a first curved portion (22a) curving outward from a center axis (21a) of the tubular body and a second curved portion (22b) curving inward to the center axis of the tubular body and positioned on a gripping portion side,
a thickness of each slit formation portion is greater than a thickness of each neck portion, t,
at a position of connection between each neck portion and each slit formation portion, a step at an opposite side to the slit is formed due to a difference in the thickness between the each slit formation portion and the each neck portion,
when the entire gripping surfaces of the gripping portions are in surface contact with each other, a surface of the step is substantially perpendicular to the center axis, and
in a state in which the gripping surfaces are in surface contact with each other, the following conditions are satisfied:

$t+g/2 \leq R$ where a radius of the cross section of the inner cavity of the tubular body is R, and a width of the slit is g;

$R-s < t+g/2 \leq R$ where a thickness of the step is s.

2. The ophthalmic forceps according to claim 1, wherein the height of the step is equal to or less than a thickness of the tubular body.

3. The ophthalmic forceps according to claim 1, wherein when the entire gripping surfaces of the gripping portions are in surface contact with each other, the surface of the step is substantially parallel to an end surface of the tubular body.

* * * * *